United States Patent [19]
McCue

[11] Patent Number: 5,976,143
[45] Date of Patent: Nov. 2, 1999

[54] ORTHOPEDIC REAMING INSTRUMENT

[75] Inventor: Diana F. McCue, Pocasset, Mass.

[73] Assignee: Johnson & Johnson Professional, Inc., Raynham, Mass.

[21] Appl. No.: 08/996,461

[22] Filed: Dec. 23, 1997

[51] Int. Cl.[6] .................................................. A61B 17/16
[52] U.S. Cl. .......................... 606/80; 408/200; 408/713
[58] Field of Search ................... 606/80, 79, 84, 606/85, 96, 97, 98, 180; 408/200, 203.5, 713

[56] References Cited

U.S. PATENT DOCUMENTS

| | | | |
|---|---|---|---|
| 5,002,547 | 3/1991 | Poggie et al. | 606/88 |
| 5,129,907 | 7/1992 | Heldreth et al. | 606/80 |
| 5,129,908 | 7/1992 | Petersen | 606/88 |
| 5,295,992 | 3/1994 | Cameron | 606/79 |
| 5,380,332 | 1/1995 | Ferrante | 606/79 |
| 5,486,177 | 1/1996 | Mumme et al. | 606/79 |
| 5,499,984 | 3/1996 | Steiner et al. | 606/80 |
| 5,520,692 | 5/1996 | Ferrante | 606/80 |
| 5,536,271 | 7/1996 | Daly et al. | 606/80 |
| 5,630,818 | 5/1997 | Del Rio et al. | 606/80 |
| 5,658,291 | 8/1997 | Techiera | 606/80 |
| 5,827,290 | 10/1998 | Bradley | 606/80 |

Primary Examiner—Michael Buiz
Assistant Examiner—David O. Reip
Attorney, Agent, or Firm—Nutter, McClennen & Fish, LLP

[57] ABSTRACT

An orthopedic reaming instrument has a generally cylindrical housing having a first end and an opposed second end, an elongate shaft extending from the first end and a removable and replaceable cutting disc disposed at the second end. The housing has a slot defined in the second end that is transverse to a longitudinal axis of the instrument and divides the second end into two spaced apart wall members having arcuate outer surfaces and opposed spaced apart inner surfaces. The cutting disc has at least one cutting edge disposed thereon and is shaped so as to mate with the wall members. A removable and replaceable drill bit may also be provided which extends from a bore in the slot through an aperture in the cutting disc.

29 Claims, 4 Drawing Sheets

ORTHOPEDIC REAMING INSTRUMENT

CROSS-REFERENCE TO RELATED APPLICATION

Not Applicable.

STATEMENT REGARDING FEDERALLY SPONSORED RESEARCH

Not Applicable.

FIELD OF THE INVENTION

The invention relates to orthopedic surgery tools, and more particularly to instrumentation to shape bone in order to accept a prosthesis.

BACKGROUND OF THE INVENTION

The patella, commonly known as the kneecap, is a hard bone having an articular surface of cartilage on the posterior side. The articular surface is held in place against the femoral condyles by the patella tendon where it provides leverage that is necessary to a properly functioning knee joint. If the articular surface becomes damaged by trauma or by degeneration, proper knee functioning breaks down, often accompanied by joint pain and immobility. In such situations, a patella prosthesis, sometimes referred to as a button, may be inserted to restore normal functioning to the knee.

Patella prostheses have also been used in total knee replacement surgery to insure a reproducible interaction of a patella with the femoral and tibial portions of the total knee replacement. Usually in such procedures the posterior side of the patella is prepared, sized and reamed so that a patella implant, when fixed to the patella, restores the reconstructed patella to its natural or original thickness.

In one procedure, the patella is prepared for the patellar implant as follows. A patellar holding clamp is placed on the patella with a clamp ring on the posterior side. The patella is then reamed with a patella reamer to a predetermined depth. One method of determining when the reamer has reached the appropriate depth involves placing a guide member on the patellar holding clamp and a stop member on the reamer. The reamer is then urged toward the patella, guided by the guide member and the clamp ring until the stop member abuts the guide member. The patellar implant is then inserted into the prepared bed.

In known patella reamers, a patella cutting surface is mounted onto a tool driver, which in turn is mounted in the chuck or collet of a portable drill or flexible powered shaft. Patella cutting surfaces are separable from their tool drivers in order to replace or sharpen the cutting edges as they are used. Tool drivers are relatively expensive, and thus must be cleaned and reused.

Some previous tool drivers grip the cutting surface by means of a flange and slot and a spring loaded ball catch or other catch devices. In some situations, the catch can trap dried blood and other debris, which can be difficult to remove during cleaning. Further, unless the tolerances of cutting surfaces and tool drivers are made very close, there can be considerable free play between the cutting surface and the tool driver. This increases wear and decreases the precision of the tool.

Additionally, because the manufacturing cost of producing these sophisticated cutting surfaces is too high for them to be disposable, the cutting surfaces being reused must be removed, cleaned, and sharpened. There is also an accompanying cost of making the cutting surface aseptic for each operation.

A patella cutting system with a disposable cutting lid is disclosed in U.S. Pat. No. 5,295,992. This patella cutting system employs a cutting lid that is secured to the tool driver by means of pins on the tool driver and slots on the cutting lid. This patella cutting system leaves a planar reamed surface in the patella and the cutting system stores cut bone debris within the tool driver behind the cutting lid. This system has disadvantages however, including difficulty in gripping the smooth surfaces of the cutting lid in order to lock or unlock the lid in a surgical setting where the surgeon is wearing gloves that are often coated with bodily or other fluids. In addition, storing bone cutting debris within the tool can lead to an increased need to remove of the cutting lid during surgery as the tool may fill up with debris. A similar cutting lid, referred to as a patellar basket, is described in U.S. Pat. No. 5,536,271.

Despite existing technology, there remains a need for a disposable cutting system useful within a patella reaming device.

SUMMARY OF THE INVENTION

The present invention provides an orthopedic instrument for reaming a patient's bone to receive a prosthesis. The instrument of the invention includes a generally cylindrical housing having a first end and a second end, an elongate shaft extending from the first end, and a removable and replaceable cutting assembly that is matable with the second end of the housing. A slot transverse to a longitudinal axis of the instrument is formed in the second end of the housing. In one embodiment, the slot divides the housing into two spaced apart wall members having opposed inner surfaces.

The cutting assembly may include a cutting disc having at least one cutting edge and a central aperture, and an elongate drill bit. The drill bit is removable and replaceable and has a proximal end and a bone penetrating distal end. The drill bit is matable within and may extend beyond the central aperture of the cutting disc. The cutting disc may mate with the second end of the housing by means of a pair of rails that mate with corresponding transverse grooves on the inner surfaces of the wall members.

The instrument of the invention may further include an axial bore effective to seat the proximal end of the drill bit and a locking element disposed on the housing and effective to selectively engage the drill bit to secure it within the axial bore. The locking element may include a transverse, elongate bore formed in the housing in communication with the axial bore and a button disposed in the transverse bore. The button is operable from outside the housing and is selectively movable between a first position, wherein the button engages the drill bit within the axial bore so as to retain the drill bit therein, and a second position wherein the button does not engage the drill bit.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
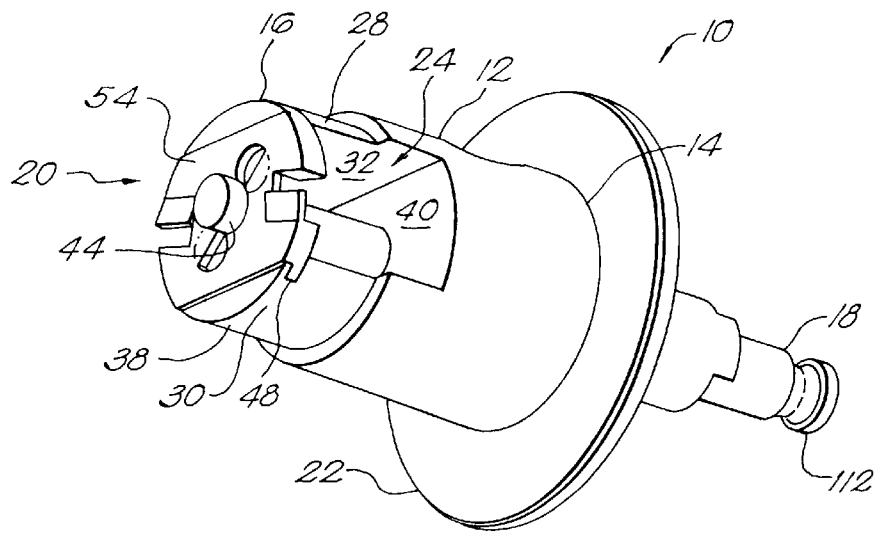
FIG. 1 is a perspective view of an orthopedic reaming instrument of the invention.

An orthopedic reaming instrument 10, shown in FIG. 1, has a generally cylindrical housing 12 having a first end 14 and an opposed second end 16, an elongate shaft 18 extending from the first end 14, and a removable and replaceable cutting assembly 20 disposed at the second end 16 of the housing 12. A stop member 22, suitable for stopping the reaming instrument 10 by abutting a guide member (not shown), may be provided at the first end 14 of the housing 12.

The housing 12, as shown in FIGS. 1 to 4, has a slot 24 formed in the second end 16 that is transverse to a longitudinal axis 26 of the instrument 10. In one embodiment the slot 24 divides the second end 16 of the housing 12 into two spaced apart wall members 28, 30 having opposed inner surfaces 32, 34 and outer surfaces 36, 38. The inner surfaces 32, 34 of exemplary housing 12 are substantially flat and parallel to each other. The outer surfaces 36, 38 of the wall members 28, 30 may have arcuate shape so that the housing 12 retains its cylindrical shape. Alternatively, the slot does not divide the second end of the housing 12 into spaced apart wall members. Instead, the slot 24 forms a single discontinuity in the wall of the housing.

Figure 3:
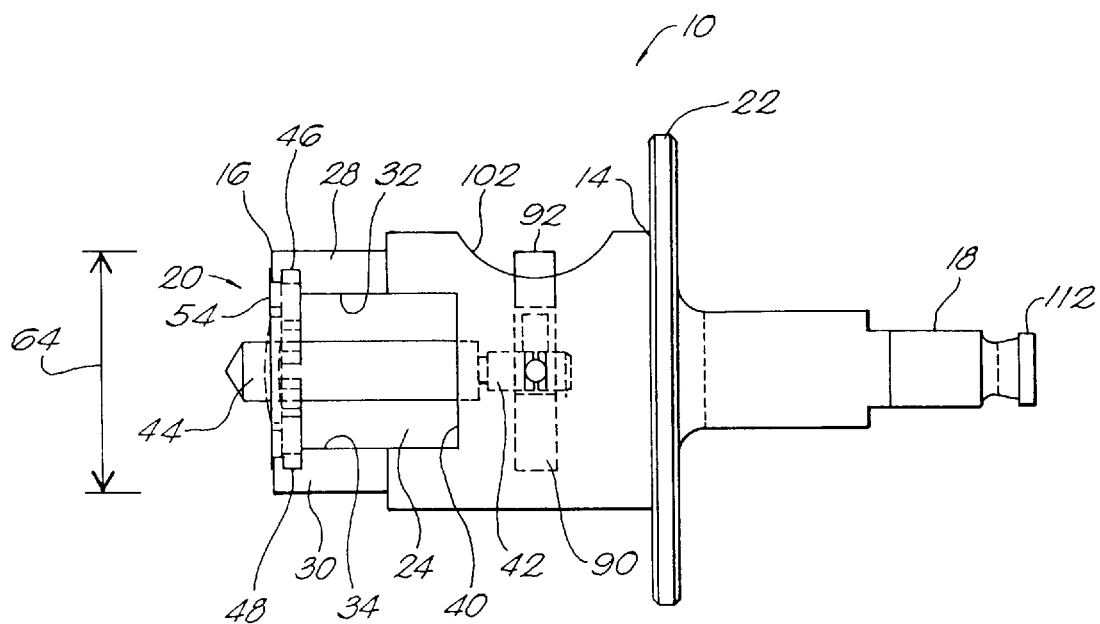
FIG. 3 is a side view of the orthopedic reaming instrument of FIG. 1.
Figure 4:
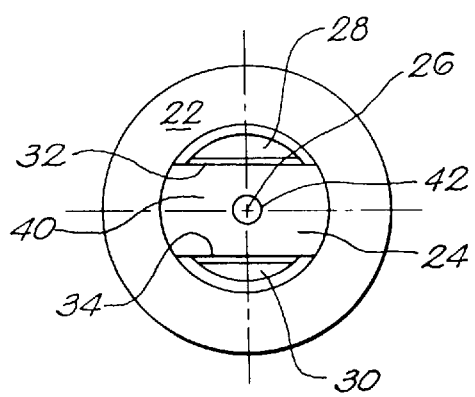
FIG. 4 is an end view of the housing of FIG. 2.

A base 40 is formed at the end of the slot 24 closest to the first end 14 of the housing 12. An axial bore 42, best seen in FIGS. 3 and 4, is provided in the base 40 along the longitudinal axis 26 of the housing 12. This axial bore 42 should be of sufficient diameter and depth to allow an elongate drill bit, such as the drill bit 44 (FIGS. 1 and 3), to removably and replaceably mate with the axial bore 42. Generally, the axial bore may be about 0.125 to 0.375 inch in diameter with a depth of about 0.25 to 0.75 inch.

To allow the cutting assembly 20 to removably and replaceably mate with the housing 12, grooves 46, 48 may be provided in a direction transverse to the longitudinal axis 26 on a distal portion of the inner surfaces 32, 34 of the wall members 28, 30 proximate to the second end 16 of the housing 12. The exact size and shape of the grooves 46, 48 may be selected by a person of ordinary skill in the art in conjunction with mating elements provided on the cutting assembly 20. Exemplary grooves 46, 48 have a height of about 0.064 inch, have a depth of about 0.0775 inch, and run along the entire length of the inner surfaces 32, 34 of the wall members 28, 30. In addition, the portions 50, 52 of the inner surfaces 32, 34 between the grooves 46, 48 and the second end 16 may be offset toward the outer surfaces 36, 38. When the mating elements of the cutting assembly 20 are similarly configured, it is impossible to mate the cutting assembly 20 to the housing 12 in an incorrect, upside-down configuration.

Figure 5:
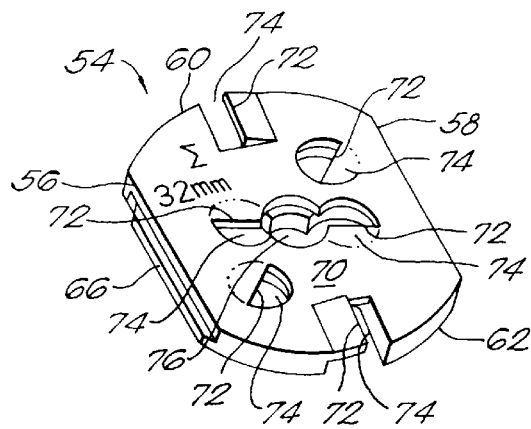
FIG. 5 is a perspective view of a distal side of a cutting disc for use with the instrument of FIG. 1.
Figure 6:
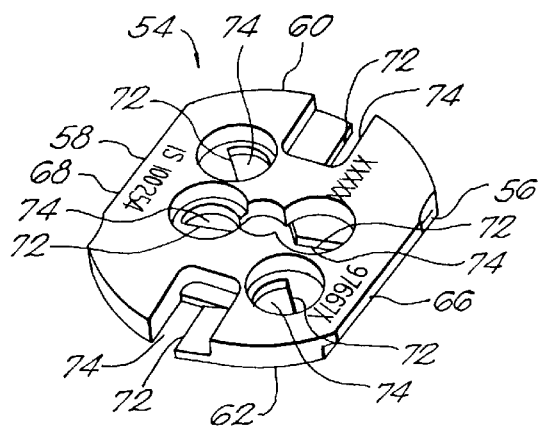
FIG. 6 is a perspective view of an opposed side of the cutting disc of FIG. 5.

Exemplary cutting assembly 20 is made up of a cutting disc 54 and an elongate drill bit 44. The cutting disc 54, shown in FIGS. 5 and 6, is shaped so as to removably and replaceably mate with the inner surfaces 32, 34 of the wall members 28, 30 proximate to the second end 16 of the housing 12. Exemplary cutting disc 20 has two opposed flat sides 56, 58 which correspond to the shape of the inner surfaces 32, 34 of the wall members 28, 30 on the housing 12. Exemplary cutting disc 54 also has two arcuate sides 60, 62. The arcuate sides 60, 62 are shaped so as to form a circular second end 16 on the housing 12 when the cutting disc 54 is mated with wall members 28, 30 having arcuate outer surfaces 36, 38. The diameter 64 (FIG. 3) of this circular second end 16 may be selected by a person of ordinary skill in the art based upon the size of the patella implant to be used in a particular operation, but may generally be between about 0.90 and 1.3 inches. A person of ordinary skill in the art will appreciate that other combinations of cutting disc 54 and wall member 28, 32 shapes and mating elements may be used within the spirit of the invention provided that the cutting assembly 20 is sufficiently secured to the housing 12 to accomplish the objectives of the invention.

Rails 66, 68 are provided on each of the flat sides 56, 58 of exemplary cutting disc 54. These rails 66, 68 are dimensioned to removably and replaceably mate with the grooves 46, 48 provided in the inner surfaces 32, 34 of the wall members 28, 30. Exemplary rails 66, 68 have a height of about 0.064 inch and a depth of about 0.0775 inch. The rails 66, 68 do not extend along the entire length of the flat sides 56, 58, but stop short of that length. Such rails allow for a similar ending in the grooves 46, 48 on the inner surfaces 32, 34 of the wall members 28, 30 so that the cutting disc 54 can only be inserted into its position in the housing 12 in one direction, and a positive stop is provided when the cutting disc 54 has reached a predetermined insertion distance and the end of at least one rail 66, 68 has reached the end of a groove 46, 48.

The cutting disc 54 has a distal, bone contacting surface 70 which faces outward from the second end 16 of the housing 12 when installed therein. The cutting disc 54 has at least one cutting edge 72; exemplary cutting disc 54 has six cutting edges 72 arranged in three opposed pairs: an inner pair, a middle pair, and a peripheral pair. Each opposed pair of cutting edges 72 is angularly offset from the other pairs. This angular offset allows the sweep of each pair of cutting edges 72 to overlap with neighboring cutting edge 72 pairs, ensuring proper reaming of the bone. While the number of cutting edges 72, as well as their specific configuration, may be determined be a person of ordinary skill in the art, generally, the cutting disc 54 will contain an even number of cutting edges 72 arranged in angularly offset pairs.

Passages 74 are provided on the cutting disc 54 adjacent to the cutting edges 72. The passages 74 are arranged so that portions of bone cut by the cutting edges 72 pass through the passages 74 into the slot 24 in a direction toward the first end 14 of the housing 12. Because the slot 24 is open between the wall members 28, 30, cut bone that passes through the passages 74 is free to exit the housing 12. The cutting disc 54 also includes a central aperture 76 that is aligned with the axial bore 42 in the housing 12. This aperture 76 is matable with the drill bit 44.

Figure 7:
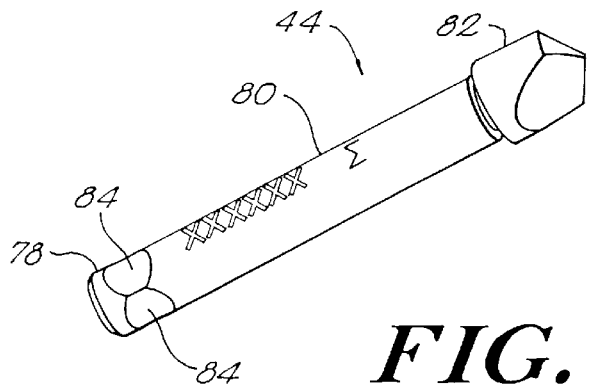
FIG. 7 is a perspective view of a drill bit for use with the instrument of FIG. 1.
Figure 8:
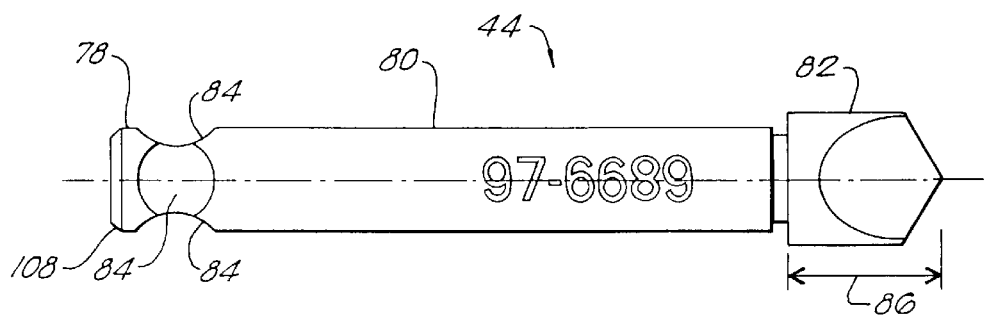
FIG. 8 is a side view of the drill bit of FIG. 7.

The cutting assembly 20 also includes removable, replaceable drill bit 44, shown in FIGS. 7 and 8, having a proximal end 78, shaft portion 80 and a bone penetrating, distal end 82. The diameter of the proximal end 78 and shaft 80 should be selected so that the drill bit 44, 76 is releasably matable within the axial bore 42 in the housing 12 and the central aperture in the cutting disc 54. Generally, the diameter of the shaft 80 may be between about 0.125 and 0.375 inch. The drill bit 44 should be long enough so that, when the drill bit 44 is releasably mated within the axial bore 42 and the central aperture 76, the drill bit 44 extends beyond the cutting disc 54 and toward the target bone. Generally, the length 86 of this extension may be between about 0.1 and 0.2 inch.

The proximal end 78 of the drill bit 44 may also have indents 84 suitable to engage a locking element within the axial bore 42. Exemplary indents 84 are arcuate and located on four sides of the shaft 80. This arrangement allows the drill bit 44 to be locked to the housing 12 against both longitudinal and rotational motion.

Figure 9:
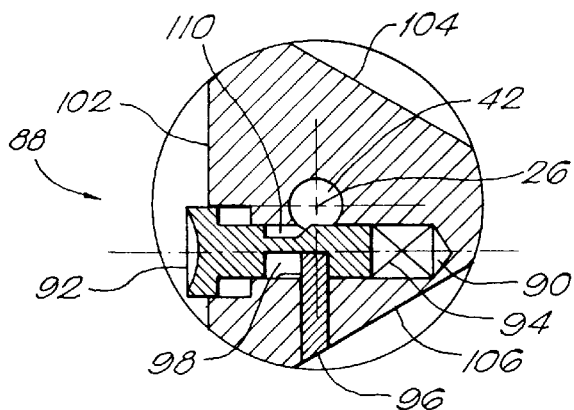
FIG. 9 is a cross sectional view of the housing of FIG. 2 taken along line 9—9 and showing a locking element.

A locking element 88, shown in FIGS. 3, 8 and 9, may be provided in the housing 12 to lock the drill bit 44 thereto. Exemplary locking element 88 includes a bore 90 formed in the housing 12 transverse to the longitudinal axis 26 and communicating with the axial bore 42, a button 92, a bias member 94, and a pin 96.

Figure 10:
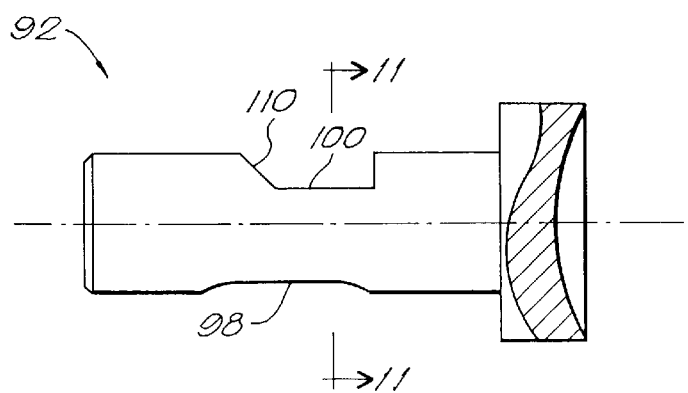
FIG. 10 is a side view, partially in section, of a locking button of the locking element of FIG. 9.
Figure 11:
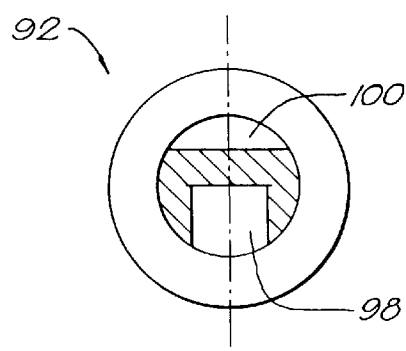
FIG. 11 is a cross sectional view of the locking button of FIG. 10 taken along line 11—11.

The button 92, also shown in FIGS. 10 and 11, is movable between a first, locked position, shown in FIG. 9, and a second, unlocked position. The pin 96, provided in the housing 12, interlocks with an elongate recess 98 formed in the button 92 to limit the movement of the button 92 between the locked and unlocked positions. The pin 96 and recess 98 interlock also prevents the button 92 from rotating within the transverse bore 90. Bias member 94, which may be a spring, biases the button 92 to the locked position. Pressing on the button 92 from outside the housing 12 moves the button 92 from the locked to the unlocked position.

In the locked position, the button 92 extends into the axial bore 42 and interlocks with one of the indents 84 provided on the shaft 80 of the drill bit 44 so as to lock the drill bit 44 longitudinally and rotationally within the housing 12. When an operator moves the button 92 to its unlocked position, a second recess 100 on the button 92 aligns with the axial bore 42 so that no part of the button 92 extends into the axial bore 42 or interlocks with the shaft 80 of the drill bit 44. Accordingly, when the button 92 is in its unlocked position, the drill bit 44 may freely slide into and out of the axial bore 42.

The button 92 extends outward from the housing 12 in its biased, locked position. Preferably, however, the button 92 should not extend beyond the circumference of the generally cylindrical housing 12. Accordingly, the button 92 may be located within a recessed region 102 on the housing 12. In the housing 12 of FIG. 3, the recessed region 12 is arcuately shaped and provided only around the button 92. In the housing 12 of FIGS. 2 and 9, the recessed region 102 is planar and is one of three recessed regions 102, 104, 106 provided symmetrically about the circumference of the housing 12. The specific arrangement of button 92 and recessed region 102 may be selected by a person of ordinary skill in the art to allow access to the locking element 88 without imparting a rotational imbalance to the housing 12 that might adversely impact the operation of the instrument 10.

The cutting disc 54 and drill bit 44 are independently replaceable as either needs replacement, due to dulling or for any other reason. To install a cutting disc 54 and drill bit 44, the cutting disc 54 is first slid into place at the second end 16 of the housing 12. The drill bit 44 is then inserted through the central aperture 76 of the cutting disc 54 and into the axial bore 42. The design of the drill bit 44 and locking element 88 may allow for the biased button 92 to move to its unlocked position due to the insertion force provided to the drill bit 44 to permit entry into the axial bore 42 and locking therein. Such a design could be realized by providing a chamfer 108 on the proximal end of the drill bit 44 (FIG. 8) and an angled wall 110 on the second recess 100 of the biased button 92 (FIGS. 9 and 10). Alternatively, the button 92 may be manually moved to its unlocked position to allow entry into the axial bore 42 by the drill bit 44, then released to its biased, locked position to lock the drill bit 44 within the axial bore 42. When locked into position in this manner, the drill bit 44 also serves to prevent the cutting disc 54 from sliding out of position by mating with the cutting disc 54 at its central aperture 76.

An operator may remove the cutting disc 54 and drill bit 44 from the housing 12 by first pressing the biased button 92 to move the button 92 from its locked to its unlocked position. The drill bit 44 can then be slid out of the axial bore 42 and through the central aperture 76 of the cutting disc 54. The cutting disc 54 then freely slides out of its position in the second end 16 of the housing 12.

Figure 2:
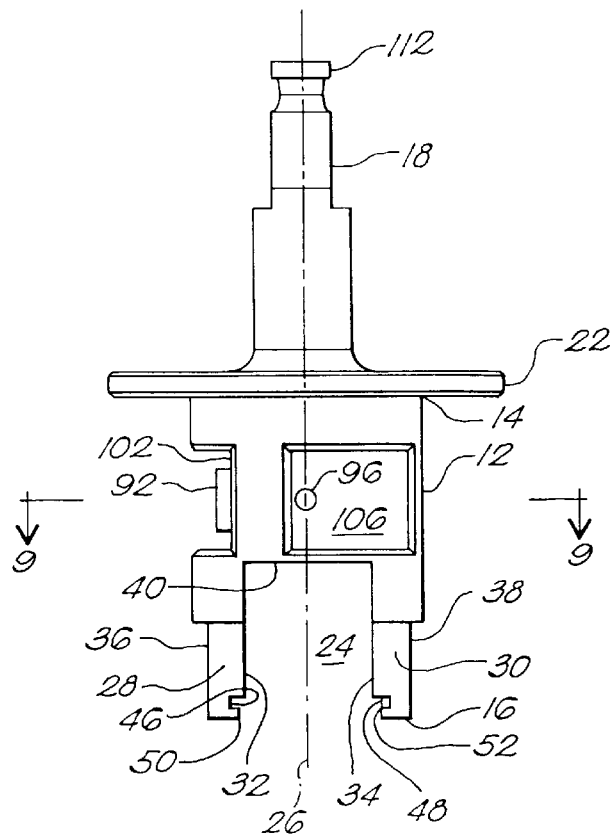
FIG. 2 is a side view of a housing and shaft of an orthopedic reaming instrument of the invention.

Elongate shaft 18, best seen in FIG. 2, may transmit rotary motion, such as from a drill, to the housing 12. Accordingly, a proximal end 112 of the shaft 18 should be engageable with a drill chuck.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. An orthopedic reaming instrument comprising:
   a generally cylindrical housing having a first end and an opposed second end that includes at least one slot that is transverse to a longitudinal axis of the instrument and that divides the second end into two spaced apart wall members having opposed inner surfaces;
   an elongate shaft suitable for transmitting rotary motion to the instrument extending from the first end; and
   a removable and replaceable cutting assembly matable with the second end of the housing and comprising a cutting disc having at least one cutting edge disposed thereon and at least one passage adjacent to the at least one cutting edge, the passage being effective to enable bone cut by the at least one cutting edge to pass through the at least one passage in a direction toward the first end of the housing.

2. The instrument of claim 1, wherein the cutting disc includes a central aperture and wherein the cutting assembly further comprises a removable and replaceable elongate drill bit having a proximal end and a bone-penetrating, distal end, the drill bit being matable within the central aperture of the cutting disc.

3. The instrument of claim 2, wherein a groove transverse to the longitudinal axis of the instrument is formed in the inner surfaces of a distal end of each wall member and the cutting disc has a pair of rails which slidably mate with the grooves.

4. The instrument of claim 3, wherein the inner surfaces of the wall members are substantially planar and are substantially parallel to each other.

5. The instrument of claim 4, wherein the wall members have accurate outer surfaces.

6. The instrument of claim 5, wherein the cutting disc has a pair of opposed arcuate sides, and a pair of opposed flat sides adjacent each of the rails, the opposed flat sides being effective to abut the inner surfaces of the wall members.

7. The instrument of claim 6, wherein the second end of the housing has a substantially circular shape when the cutting disc is mated with the wall members.

8. The instrument of claim 7, wherein an outer diameter of the second end is between about 0.9 and 1.3 inches.

9. The instrument of claim 2, wherein the cutting disc includes two cutting edges.

10. The instrument of claim 2, wherein the cutting disc includes four cutting edges.

11. The instrument of claim 10, wherein the cutting edges are arranged into an inner opposed pair and a peripheral opposed pair that is angularly offset from the inner opposed pair.

12. The instrument of claim 2, wherein the cutting disc includes six cutting edges.

13. The instrument of claim 12, wherein the cutting edges are arranged into an inner opposed pair, a middle opposed pair and a peripheral opposed pair, each pair being angularly offset with respect to the other pairs.

14. The instrument of claim 2, wherein the cutting disc and the drill bit are independently removable and replaceable.

15. The instrument of claim 14, wherein the proximal end of the drill bit is releasably mated to the housing and the drill bit extends through and protrudes from the central aperture of the cutting disc.

16. The instrument of claim 15, wherein the drill bit extends approximately 0.1 to 0.2 inch beyond a distal surface of the cutting disc.

17. The instrument of claim 14, further comprising:
    an axial bore formed in the housing along the longitudinal axis thereof, the axial bore having an opening facing the second end of the housing and being effective to seat the proximal end of the drill bit while allowing the distal end of the drill bit to extend through and protrude from the central aperture; and
    a locking element disposed on the housing and effective to selectively engage the drill bit to secure it within the axial bore.

18. The instrument of claim 17, where in the locking element includes an elongate bore formed in the housing in a direction transverse to the longitudinal axis and communicating with the axial bore, and a button disposed in the transverse bore, the button being operable from outside the housing and selectively movable between a first position wherein the button engages the drill bit within the axial bore so as to retain the drill bit therein, and a second position wherein the button does not engage the drill bit.

19. The instrument of claim 1, wherein the at least one passage opens into the slot in the housing so that bone cut by the at least one cutting edge may exit the housing.

20. The instrument of claim 1, wherein the elongate shaft of the reaming instrument has a proximal end that is engageable with a drill chuck.

21. An orthopedic reaming instrument comprising:
    a generally cylindrical housing having a first end and an opposed second end that includes a slot that is transverse to a longitudinal axis of the tool, the slot having a base with an axial bore formed therein, the slot dividing the second end into two spaced apart wall members having arcuate outer surfaces and opposed, spaced apart inner surfaces;
    an elongate shaft extending from the first end and being effective to transmit rotary motion to the instrument extending from the first end;
    a removable and replaceable cutting disc matable between the wall members of the housing, the cutting disc having an aperture formed therein and at least one cutting edge disposed thereon; and
    a removable and replaceable drill bit releasably matable within the axial bore at the base of the slot in the housing and extending axially through the aperture formed in the cutting disc.

22. The instrument of claim 21, wherein the inner surface of each wall member, at a distal end thereof, has a groove that is transverse to the longitudinal axis of the instrument.

23. The instrument of claim 22, wherein the cutting disc has opposed flat sides wherein each flat side has a rail matable within the grooves of the wall members.

24. The instrument of claim 21, wherein the inner surfaces of the wall members are substantially planar and are substantially parallel to each other.

25. The instrument of claim 21, wherein an outside diameter of the second end is between about 0.9 and 1.3 inches.

26. The instrument of claim 21, wherein the cutting disc includes at least one passage adjacent to the at least one cutting edge so that bone cut by the at least one cutting edge is able to pass through the at least one passage in a direction toward the first end of the housing.

27. The instrument of claim 26, wherein the at least one passage opens into the slot in the housing so that bone cut by the at least one cutting edge may exit the housing.

28. The instrument of claim 21, wherein the elongate shaft is selectively matable with a power reaming instrument.

29. The instrument of claim 21, further including a locking device disposed on the housing and effective to selectively engage the drill bit to secure the drill bit within the axial bore of the housing.

* * * * *